United States Patent
McIlrath

(10) Patent No.: US 9,546,973 B2
(45) Date of Patent: Jan. 17, 2017

(54) PEAK OFFSET CORRECTION FOR ANALYTE TEST STRIP

(75) Inventor: Joanne McIlrath, Inverness (GB)

(73) Assignee: LifeScan Scotland Limited, Inverness (GB)

( * ) Notice: Subject to any disclaimer, the term of this patent is extended or adjusted under 35 U.S.C. 154(b) by 307 days.

(21) Appl. No.: 14/119,410

(22) PCT Filed: May 25, 2012

(86) PCT No.: PCT/GB2012/051192
§ 371 (c)(1),
(2), (4) Date: Mar. 10, 2014

(87) PCT Pub. No.: WO2012/164271
PCT Pub. Date: Dec. 6, 2012

(65) Prior Publication Data
US 2014/0202882 A1    Jul. 24, 2014

Related U.S. Application Data

(60) Provisional application No. 61/491,008, filed on May 27, 2011.

(51) Int. Cl.
 *G01N 27/327* (2006.01)
(52) U.S. Cl.
 CPC ...... *G01N 27/3271* (2013.01); *G01N 27/3274* (2013.01)
(58) Field of Classification Search
 CPC .................................. G01N 27/327–27/3274
 See application file for complete search history.

(56) References Cited

U.S. PATENT DOCUMENTS

| | | | |
|---|---|---|---|
| 5,942,102 A | 8/1999 | Hodges et al. | |
| 6,413,411 B1* | 7/2002 | Pottgen ............. | G01N 27/3273 205/775 |
| 6,525,549 B1 | 2/2003 | Poellmann | |
| 7,468,125 B2 | 12/2008 | Kraft et al. | |
| 7,645,374 B2* | 1/2010 | Diamond ............... | C12Q 1/006 204/403.03 |
| 2005/0067301 A1 | 3/2005 | Morita et al. | |
| 2007/0087397 A1 | 4/2007 | Kraft et al. | |
| 2007/0227912 A1 | 10/2007 | Chatelier et al. | |
| 2007/0272564 A1 | 11/2007 | Huang | |
| 2009/0301899 A1 | 12/2009 | Hodges et al. | |
| 2011/0005941 A1 | 1/2011 | Blythe et al. | |

FOREIGN PATENT DOCUMENTS

| | | |
|---|---|---|
| CN | 1570614 A | 1/2005 |
| CN | 1589400 A | 3/2005 |
| CN | 1996000 A | 7/2007 |

(Continued)

OTHER PUBLICATIONS

JPO computer-generated English language translation of JP 2007-271622A. Downloaded Sep. 2, 2016.*

(Continued)

*Primary Examiner* — Alexander Noguerola

(57) ABSTRACT

Measurement with a test strip having two working electrodes (12, 14), using the current transient (402, 404) for each working electrode measured at a predetermined durational offset (Tpred1, Tpred2) from a peak (408, 410) of the current transient.

15 Claims, 8 Drawing Sheets

(56) References Cited

FOREIGN PATENT DOCUMENTS

| CN | 101078719 A | 11/2007 |
|---|---|---|
| EP | 1775587 A2 | 4/2007 |
| EP | 1783486 A1 | 5/2007 |
| EP | 1775587 B1 | 10/2013 |
| JP | 2000500571 A | 1/2000 |
| JP | 2007271622 A | 10/2007 |

OTHER PUBLICATIONS

JPO computer-generated English language translation of JP 2000-500571 A. Downloaded Sep. 2, 2016.*
Patent Examination Report No. 1 issued in related Australian Patent Application No. 2012264417, dated Feb. 25, 2014, 3 pages.
First Office Action issued in related Chinese Patent Application No. 2012800259867, dated Oct. 21, 204, 18 pages.
Search Report issued in related Chinese Patent Application No. 2012800259867, dated Oct. 13, 204, 2 pages.
Search Report issued in related European Patent Application No. 12729694.5, dated Sep. 15, 2014, 4 pages.
International Search Report and Written Opinion issued in related International Patent Application No. PCT/GB2012/051192, dated Sep. 4, 2012, 11 pages.
Notice of Reasons for Rejection issued in related Japanese Patent Application No. 2014-513243, dated Apr. 26, 2016, 6 pages.
Official Action issued in related Russian Patent Application No. 2013158387, dated May 30, 2016, 14 pages.

* cited by examiner

PEAK OFFSET CORRECTION FOR ANALYTE TEST STRIP

This application claims the benefits under 35 USC§§119, 120, 365, and 371 of prior filed provisional application Ser. No. 61/491,008 filed on May 27, 2011, and International Patent Application PCT/GB2012/051192 filed on May 25, 2012, which applications are incorporated by reference in their entirety hereinto this application as if fully set forth herein.

BACKGROUND

Electrochemical glucose test strips, such as those used in the OneTouch® Ultra® whole blood testing kit, which is available from LifeScan, Inc., are designed to measure the concentration of glucose in a blood sample from patients with diabetes. The measurement of glucose can be based on the selective oxidation of glucose by the enzyme glucose oxidase (GO). The reactions that can occur in a glucose test strip are summarized below in Equations 1 and 2.

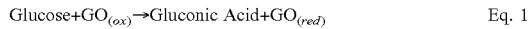

Glucose+$GO_{(ox)}$→Gluconic Acid+$GO_{(red)}$    Eq. 1

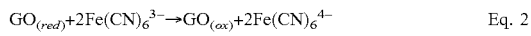

$GO_{(red)}$+2Fe(CN)$_6^{3-}$→$GO_{(ox)}$+2Fe(CN)$_6^{4-}$    Eq. 2

As illustrated in Equation 1, glucose is oxidized to gluconic acid by the oxidized form of glucose oxidase ($GO_{(ox)}$). It should be noted that $GO_{(ox)}$ may also be referred to as an "oxidized enzyme." During the reaction in Equation 1, the oxidized enzyme $GO_{(ox)}$ is converted to its reduced state, which is denoted as $GO_{(red)}$ (i.e., "reduced enzyme"). Next, the reduced enzyme $GO_{(red)}$ is re-oxidized back to $GO_{(ox)}$ by reaction with Fe(CN)$_6^{3-}$ (referred to as either oxidized mediator or ferricyanide) as illustrated in Equation 2. During the re-generation of $GO_{(red)}$ back to its oxidized state $GO_{(ox)}$, Fe(CN)$_6^{3-}$ is reduced to Fe(CN)$_6^{4-}$ (referred to as either reduced mediator or ferrocyanide).

When the reactions set forth above are conducted with a test voltage applied between two electrodes, a test current can be created by the electrochemical re-oxidation of the reduced mediator at the electrode surface. Thus, since, in an ideal environment, the amount of ferrocyanide created during the chemical reaction described above is directly proportional to the amount of glucose in the sample positioned between the electrodes, the test current generated would be proportional to the glucose content of the sample. A mediator, such as ferricyanide, is a compound that accepts electrons from an enzyme such as glucose oxidase and then donates the electrons to an electrode. As the concentration of glucose in the sample increases, the amount of reduced mediator formed also increases; hence, there is a direct relationship between the test current, resulting from the re-oxidation of reduced mediator, and glucose concentration. In particular, the transfer of electrons across the electrical interface results in the flow of a test current (2 moles of electrons for every mole of glucose that is oxidized). The test current resulting from the introduction of glucose can, therefore, be referred to as a glucose current.

Because it can be very important to know the concentration of glucose in blood, particularly in people with diabetes, test meters have been developed using the principals set forth above to enable the average person to sample and test their blood for determining their glucose concentration at any given time. The glucose current generated is detected by the test meter and converted into a glucose concentration reading using an algorithm that relates the test current to a glucose concentration via a simple mathematical formula. In general, the test meters work in conjunction with a disposable test strip that may include a sample-receiving chamber and at least two electrodes disposed within the sample-receiving chamber in addition to the enzyme (e.g. glucose oxidase) and the mediator (e.g. ferricyanide). In use, the user pricks their finger or other convenient site to induce bleeding and introduces a blood sample to the sample-receiving chamber, thus starting the chemical reaction set forth above.

SUMMARY OF THE DISCLOSURE

Applicants have discovered various embodiments of a technique to allow for improved accuracy in the measurement of an analyte, principally, by measuring a current value at a temporal offset from a peak or maxima of the current transient generated by an electrochemical reaction of the analyte. In particular, one aspect of the invention includes a method of determining analyte concentration in physiological fluid. The method may be achieved by: providing a reagent disposed between two electrodes; depositing a physiological fluid on the reagent; causing a physical transformation of an analyte in the physiological fluid into a different form and generate a current transient from each of the electrode; determining a peak in the current transient for each of the electrodes; measuring a value of the current transient at a predetermined temporal offset from the peak of each current transient from each of the electrodes; and calculating the analyte concentration from the measured current values of the electrodes in the measuring step. In a further variation of the method, each of the predetermined temporal offsets comprises about 3.3 seconds for one of the electrodes and about 2.5 seconds for the other electrode; the measured current value from one of the electrodes is summed together with the measured current value of the other electrode; or the analyte comprises glucose and the physiological fluid comprises blood.

In yet a further aspect, a method of determining analyte concentration in physiological fluid. The method may be achieved by: providing a substrate in which a reagent is disposed between two electrodes; depositing a physiological fluid onto the reagent; applying an electrical potential to the electrodes to transform an analyte in the physiological fluid into a different form and generate a current transient from each of the electrode; determining a peak in the current transient for each of the electrodes; measuring a current value of the current transient at a predetermined temporal offset from the peak of each current transient from each of the electrodes; and calculating the analyte concentration from the measured current values of the electrodes in the measuring step. In a further implementation of this method, each of the predetermined temporal offsets comprises about 3.3 seconds for one of the electrodes and about 2.5 seconds for the other electrode; the measured current value from one of the electrodes is summed together with the measured current value of the other electrode; or the analyte comprises glucose and the physiological fluid comprises blood.

In another aspect, a glucose measurement system to measure an analyte concentration in physiological fluid of a user is provided. The system includes a test strip and an analyte meter. The test strip includes a first working electrode, a second working electrode and a reagent layer having a mediator in a test area disposed proximate the first and second working electrodes. The electrodes are connected to corresponding contact pads. The analyte meter has a microprocessor and a test circuit in connection with a test strip port that electrically connects the contact pads of the test strip so that, when the test strip is inserted into the test strip port with physiological fluid deposited in the test area, the meter is configured to apply a voltage potential over a duration and measure a current value of a current transient for each electrode at a predetermined duration after a peak of the current transient, the current value being representative of the analyte concentration. In a further implementation of the system, each of the predetermined duration comprises about 3.3 seconds for one of the electrodes and about 2.5 seconds for the other electrode; the measured current value from one of the electrodes is summed together with the measured current value of the other electrode; the analyte comprises glucose and the physiological fluid comprises blood.

In each of the aspects described above, the following features can also be combined thereto to obtain alternative aspects of the invention. For example, the temporal offset for one electrode may be a first time offset from the peak of the current transient of the one electrode and the temporal offset from the peak of the current transient of the other electrode may be a second time offset different from the first time offset; the first time offset is greater than the second time offset by about 25%; and the predetermined duration for one electrode may be a first time offset from the peak of the current transient of the one electrode and the predetermined duration from the peak of the current transient of the other electrode may be a second time offset different from the first time offset.

These and other embodiments, features and advantages will become apparent to those skilled in the art when taken with reference to the following more detailed description of the exemplary embodiments of the invention in conjunction with the accompanying drawings that are first briefly described.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention (wherein like numerals represent like elements), in which.

MODES OF CARRYING OUT THE INVENTION

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. In addition, as used herein, the terms "patient", "host" and "subject" refer to any human or animal subject and are not intended to limit the systems or methods to human use, although use of the subject invention in a human patient represents a preferred embodiment.

Figure 1:
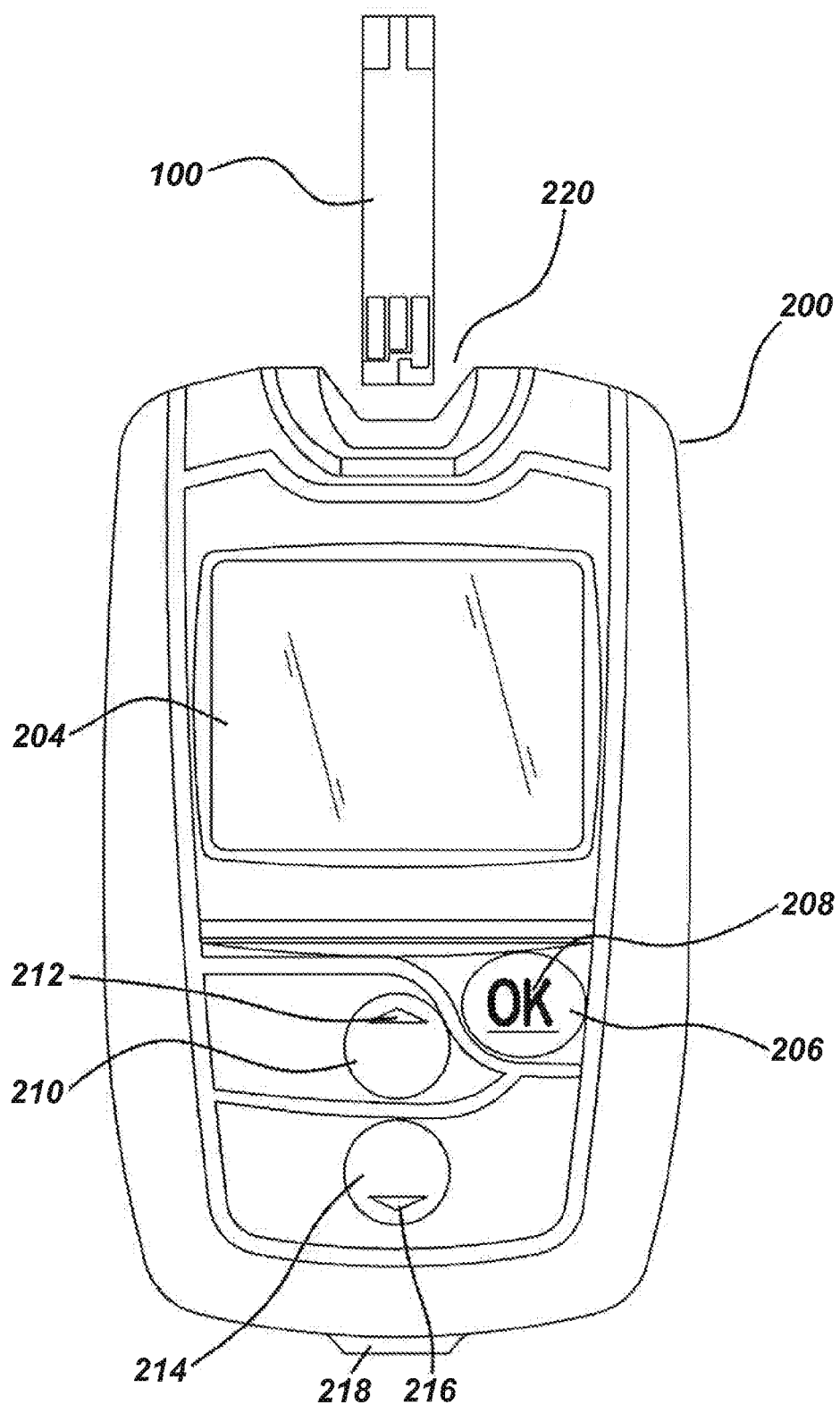
FIG. 1 illustrates an analyte measurement system.

FIG. 1 illustrates a test meter 200, for testing glucose levels in the blood of an individual with a test strip produced by the methods and techniques illustrated and described herein. Test meter 200 may include user interface inputs (206, 210, 214), which can be in the form of buttons, for entry of data, navigation of menus, and execution of commands. Data can include values representative of analyte concentration, and/or information that are related to the everyday lifestyle of an individual. Information, which is related to the everyday lifestyle, can include food intake, medication use, the occurrence of health check-ups, general health condition and exercise levels of an individual. Test meter 200 can also include a display 204 that can be used to report measured glucose levels, and to facilitate entry of lifestyle related information.

Test meter 200 may include a first user interface input 206, a second user interface input 210, and a third user interface input 214. User interface inputs 206, 210, and 214 facilitate entry and analysis of data stored in the testing device, enabling a user to navigate through the user interface displayed on display 204. User interface inputs 206, 210, and 214 include a first marking 208, a second marking 212, and a third marking 216, which help in correlating user interface inputs to characters on display 204.

Test meter 200 can be turned on by inserting a test strip 100 into a strip port connector 220, by pressing and briefly holding first user interface input 206, or by the detection of data traffic across a data port 218. Test meter 200 can be switched of by removing test strip 100, pressing and briefly holding first user interface input 206, navigating to and selecting a meter off option from a main menu screen, or by not pressing any buttons for a predetermined time. Display 104 can optionally include a backlight.

In one embodiment, test meter 200 can be configured to not receive a calibration input for example, from any external source, when switching from a first test strip batch to a second test strip batch. Thus, in one exemplary embodiment, the meter is configured to not receive a calibration input from external sources, such as a user interface (such as inputs 206, 210, 214), an inserted test strip, a separate code key or a code strip, data port 218. Such a calibration input is not necessary when all of the test strip batches have a substantially uniform calibration characteristic. The calibration input can be a set of values ascribed to a particular test strip batch. For example, the calibration input can include a batch slope and a batch intercept value for a particular test strip batch. The calibrations input, such as batch slope and intercept values, may be preset within the meter as will be described below.

Figure 2:
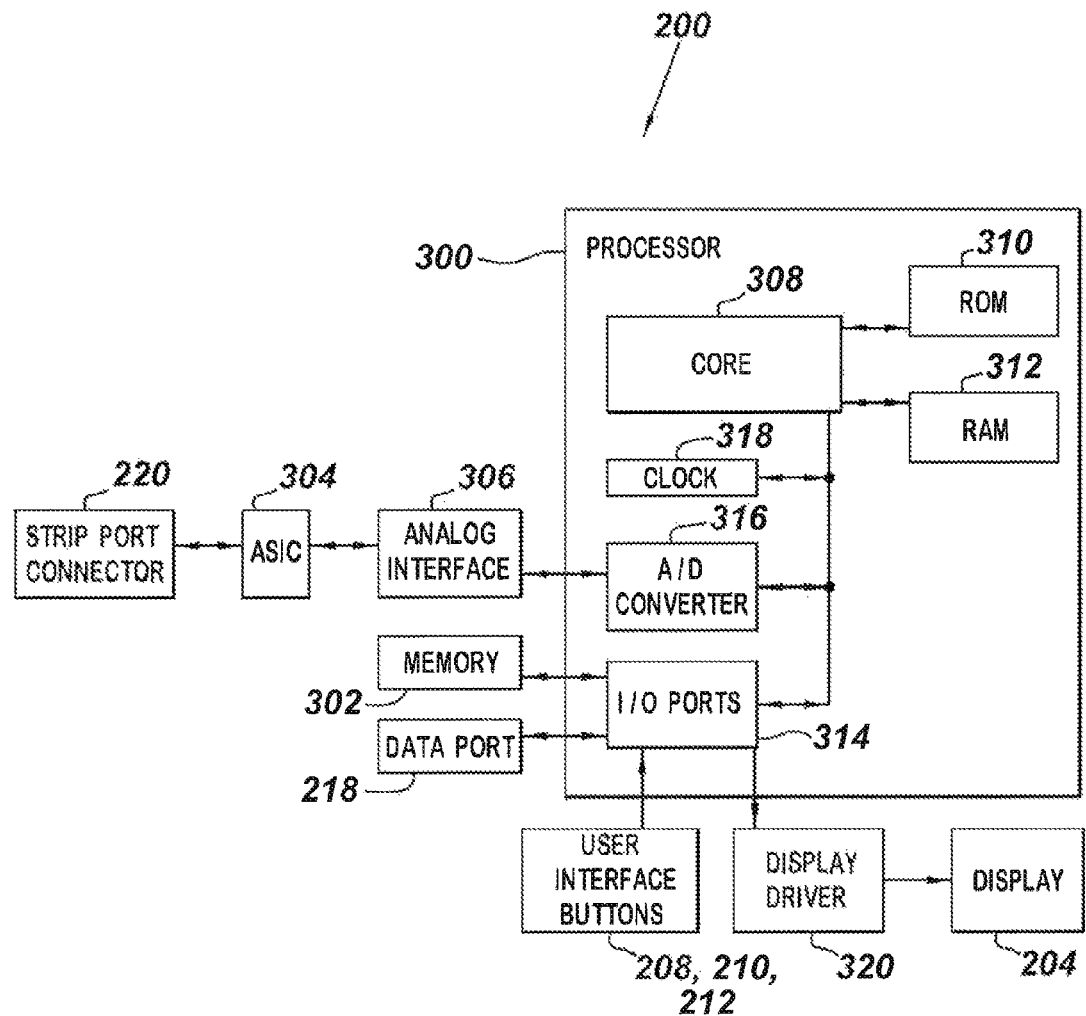
FIG. 2 illustrates in simplified schematic form the components of the meter 200.

Referring to FIG. 2, an exemplary internal layout of test meter 200 is shown. Test meter 200 may include a processor 300, which in some embodiments described and illustrated herein is a 32-bit RISC microcontroller. In the preferred embodiments described and illustrated herein, processor 300 is preferably selected from the MSP 430 family of ultra-low power microcontrollers manufactured by Texas Instruments of Dallas, Tex. The processor can be bi-directionally connected via I/O ports 314 to a memory 302, which in some embodiments described and illustrated herein is an EEPROM. Also connected to processor 300 via I/O ports 214 are the data port 218, the user interface inputs 206, 210, and 214, and a display driver 320. Data port 218 can be connected to processor 300, thereby enabling transfer of data between memory 302 and an external device, such as a personal computer. User interface inputs 206, 210, and 214 are directly connected to processor 300. Processor 300 controls display 204 via display driver 320. Memory 302 may be pre-loaded with calibration information, such as batch slope and batch intercept values, during production of test meter 200. This pre-loaded calibration information can be accessed and used by processor 300 upon receiving a suitable signal (such as current) from the strip via strip port connector 220 so as to calculate a corresponding analyte level (such as blood glucose concentration) using the signal and the calibration information without receiving calibration input from any external source.

In embodiments described and illustrated herein, test meter 200 may include an Application Specific Integrated Circuit (ASIC) 304, so as to provide electronic circuitry used in measurements of glucose level in blood that has been applied to a test strip 100 inserted into strip port connector 220. Analog voltages can pass to and from ASIC 304 by way of an analog interface 306. Analog signals from analog interface 306 can be converted to digital signals by an A/D converter 316. Processor 300 further includes a core 308, a ROM 310 (containing computer code), a RAM 312, and a clock 318. In one embodiment, the processor 300 is configured (or programmed) to disable all of the user interface inputs except for a single input upon a display of an analyte value by the display unit such as, for example, during a time period after an analyte measurement. In an alternative embodiment, the processor 300 is configured (or programmed) to ignore any input from all of the user interface inputs except for a single input upon a display of an analyte value by the display unit.

Figure 3A:
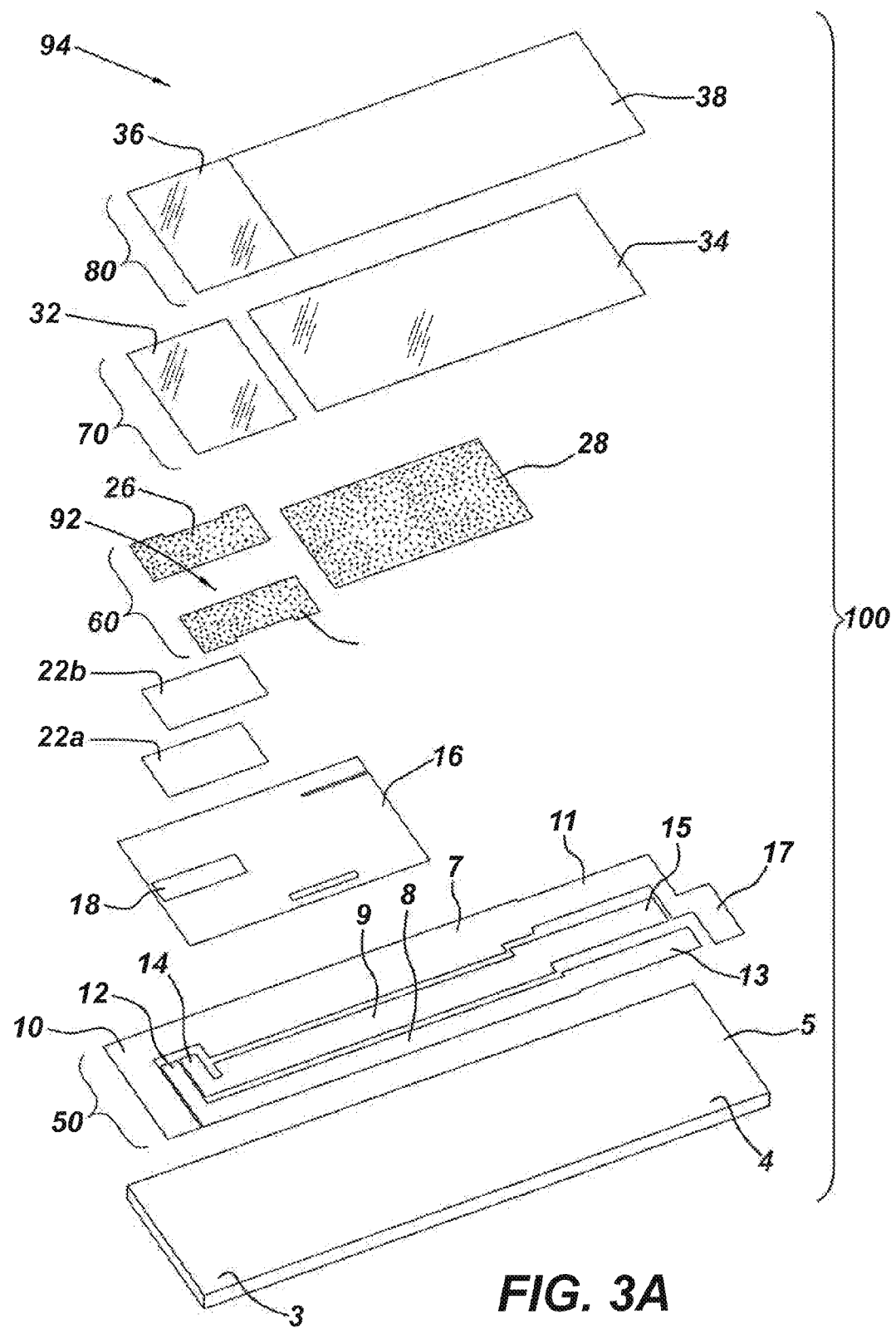
FIG. 3A illustrates the test strip 100 of the system of FIG. 1.

FIG. 3A is an exemplary exploded perspective view of a test strip 100, which may include seven layers disposed on a substrate 5. The seven layers disposed on substrate 5 can be a conductive layer 50 (which can also be referred to as electrode layer 50), an insulation layer 16, two overlapping reagent layers 22a and 22b, an adhesive layer 60 which includes adhesive portions 24, 26, and 28, a hydrophilic layer 70, and a top layer 80. Test strip 100 may be manufactured in a series of steps where the conductive layer 50, insulation layer 16, reagent layers 22, adhesive layer 60 are sequentially deposited on substrate 5 using, for example, a screen-printing process. Hydrophilic layer 70 and top layer 80 can be disposed from a roll stock and laminated onto substrate 5 as either an integrated laminate or as separate layers. Test strip 100 has a distal portion 3 and a proximal portion 4 as shown in FIG. 3A.

Test strip 100 may include a sample-receiving chamber 92 through which a blood sample may be drawn. Sample-receiving chamber 92 can include an inlet at a proximal end and an outlet at the side edges of test strip 100, as illustrated in FIG. 3A. A blood sample 94 can be applied to the inlet to fill a sample-receiving chamber 92 so that glucose can be measured. The side edges of a first adhesive pad 24 and a second adhesive pad 26 located adjacent to reagent layer 22 each define a wall of sample-receiving chamber 92, as illustrated in FIG. 3A. A bottom portion or "floor" of sample-receiving chamber 92 may include a portion of substrate 5, conductive layer 50, and insulation layer 16, as illustrated in FIG. 3A. Atop portion or "roof" of sample-receiving chamber 92 may include distal hydrophilic portion 32, as illustrated in FIG. 3A.

For test strip 100, as illustrated in FIG. 3A, substrate 5 can be used as a foundation for helping support subsequently applied layers. Substrate 5 can be in the form of a polyester sheet such as a polyethylene tetraphthalate (PET) material (Hostaphan PET supplied by Mitsubishi). Substrate 5 can be in a roll format, nominally 350 microns thick by 370 millimeters wide and approximately 60 meters in length.

A conductive layer is required for forming electrodes that can be used for the electrochemical measurement of glucose. Conductive layer 50 can be made from a carbon ink that is screen-printed onto substrate 5. In a screen-printing process, carbon ink is loaded onto a screen and then transferred through the screen using a squeegee. The printed carbon ink can be dried using hot air at about 140° C. The carbon ink can include VAGH resin, carbon black, graphite (KS15), and one or more solvents for the resin, carbon and graphite mixture. More particularly, the carbon ink may incorporate a ratio of carbon black:VAGH resin of about 2.90:1 and a ratio of graphite:carbon black of about 2.62:1 in the carbon ink.

Figure 3B:
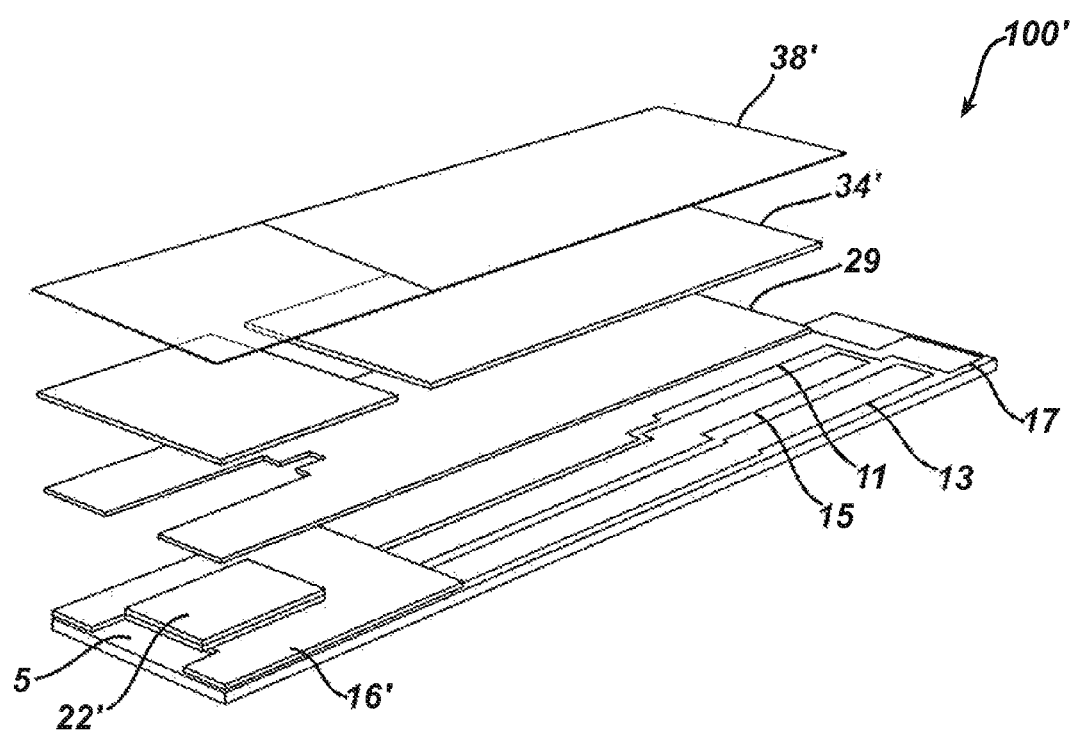
FIG. 3B illustrates an alternate test strip 100' for the system of FIG. 1.

For test strip 100, as illustrated in FIG. 3A, conductive layer 50 may include a reference electrode 10, a first working electrode 12, a second working electrode 14, a first contact pad 13, a second contact pad 15, a reference contact pad 11, a first working electrode track 8, a second working electrode track 9, a reference electrode track 7, and a strip detection bar 17. The conductive layer may be formed from carbon ink. First contact pad 13, second contact pad 15, and reference contact pad 11 may be adapted to electrically connect to a test meter. First working electrode track 8 provides an electrically continuous pathway from first working electrode 12 to first contact pad 13. Similarly, second working electrode track 9 provides an electrically continuous pathway from second working electrode 14 to second contact pad 15. Similarly, reference electrode track 7 provides an electrically continuous pathway from reference electrode 10 to reference contact pad 11. Strip detection bar 17 is electrically connected to reference contact pad 11. A test meter can detect that test strip 100 has been properly inserted by measuring a continuity between reference contact pad 11 and strip detection bar 17, as illustrated in FIG. 3A. An alternate version of the test strip 100 is shown in FIG. 3B as strip 100'. In this version, the top layer 38', hydrophilic film layer 34' and spacer 29 have been combined together to form an integrated assembly for mounting to the substrate 5 with reagent layer 22' disposed proximate insulation layer 16'.

Figure 4A:
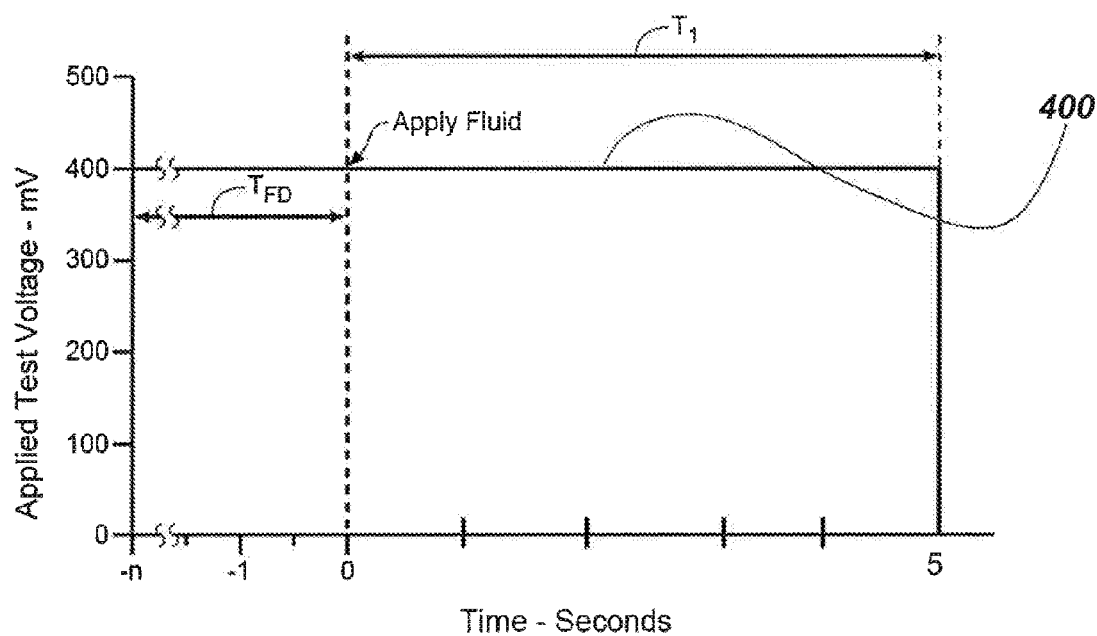
FIG. 4A illustrates a graph of time over applied potential to the test strip of FIG. 1.

FIG. 4A is an exemplary chart of a test voltage applied to test strip 100. Before a fluid sample is applied to test strip 100, test meter 200 is in a fluid detection mode in which a first test voltage of about 400 millivolts is applied between second working electrode 14 and reference electrode 10. A second test voltage of about 400 millivolts is preferably applied simultaneously between first working electrode 12 and reference electrode 10. Alternatively, the second test voltage may also be applied contemporaneously such that a time interval of the application of the first test voltage overlaps with a time interval in the application of the second test voltage. The test meter may be in a fluid detection mode during fluid detection time interval $t_{FD}$ prior to the detection of physiological fluid at starting time at zero. In the fluid detection mode, test meter 200 determines when a fluid is applied to test strip 100 such that the fluid wets second working electrode 14 and reference electrode 10. Once test meter 200 recognizes that the physiological fluid has been applied because of, for example, a sufficient increase in the measured test current at second working electrode 14, test meter 200 assigns a zero second marker at zero time "0" and starts the test time interval $T_1$. Upon the completion of the test time interval 71 the test voltage is removed. For simplicity, FIG. 4A only shows the first test voltage applied to test strip 100.

Hereafter, a description of how glucose concentration is determined from the known current transients (i.e., the measured electrical current response in nanoamperes as a function of time) that are measured when the test voltages of FIG. 4A are applied to the known test strip 100.

In FIG. 4A, the first and second test voltages applied to test strip 100 are generally from about +100 millivolts to about +600 millivolts. In one embodiment in which the electrodes include carbon ink and the mediator is ferricyanide, the test voltage is about +400 millivolts. Other mediator and electrode material combinations will require different test voltages. The duration of the test voltages is generally from about 2 to about 4 seconds after a reaction period and is typically about 3 seconds after a reaction period. Typically, time $T_1$ is measured relative to time $t_0$. As the voltage 400 is maintained in FIG. 4A for the duration of T1, the current transient 402 for the first working electrode is generated starting at zero time and likewise the current transient 404 for the second working electrode is also generated with respect to the zero time. The current transients build up to a peak proximate peak time Tp at which time, the current slowly drops off until approximately 5 seconds after zero time. At the point 406, the current value for each of the working electrodes are measured and added together. From knowledge of the calibration code offset and slope for the particular test strip 100, the glucose concentration can be calculated. "Intercept" and "Slope" are the values obtained by measuring calibration data from a batch of test strips. Typically around 1500 strips are selected at random from the lot or batch. Body fluid from donors is spiked to various analyte levels, typically six different glucose concentrations. Typically, blood from 12 different donors is spiked to each of the six levels. Eight strips are given blood from identical donors and levels so that a total of 12×6×8=576 tests are conducted for that lot. These are benchmarked against actual analyte level (e.g., blood glucose concentration) by measuring these using a standard laboratory analyzer such as Yellow Springs Instrument (YSI). A graph of measured glucose concentration is plotted against actual glucose concentration (or measured current versus YSI current), A graph of measured glucose concentration is plotted against actual glucose concentration (or measured current versus YSI current), and a formula y=mx+c least squares fitted to the graph to give a value for batch slope m and batch intercept c for the remaining strips from the lot or batch.

Figure 4B:
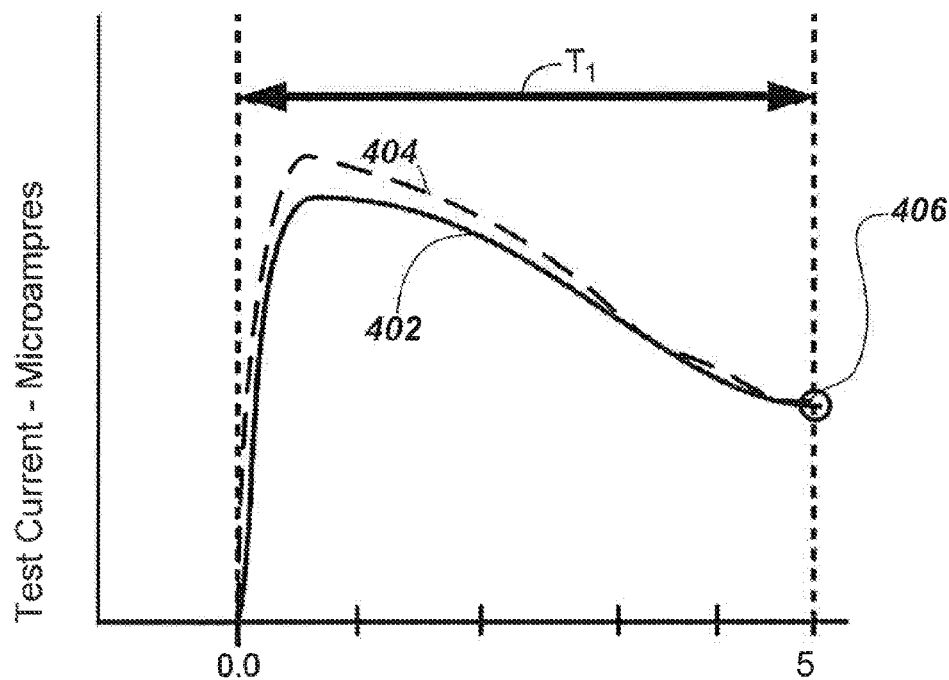
FIG. 4B illustrates a graph of time over output current from the test strip of FIG. 1.

As an example of an analyte calculation (e.g., glucose) for strip 100 (FIG. 3A), it is assumed in FIG. 4B that the sampled current value at 406 for the first working electrode is 1600 nanoamps whereas the current value at 406 for the second working electrode is 1300 nanoamps and for the calibration code of the test strip the Intercept is 500 nanoamps and the Slope is 18 nanoamp/mg/dL. Glucose concentration G can be thereafter be determined from Equation 3 as follow:

$$G=[(I_{we1}+I_{we2})-\text{Intercept}]/\text{Slope} \qquad \text{Eq. 3}$$

Where
$I_{we1}$ is the current measured for the first working electrode at the end of T1;
$I_{we2}$ is the current measured for the second working electrode at the end of T1;
Slope is the value obtained from calibration testing of a batch of test strip of which this particular strip comes from;
Intercept is the value obtained from calibration testing of a batch of test strip of which this particular strip comes from.

From Eq. 3 G=[(1600+1300)−500]/18 and therefore, G=133.33 nanoamp~133 mg/dL.

It is noted that certain offsets may be provided to the current value Iwe1 and Iwe2 to account for errors or delay time in the electrical circuit of the meter 200. Temperature compensation can also be utilized to ensure that the results are calibrated to a referential temperature such as for example room temperature of about 20 degrees Celsius.

Applicant has discovered that for blood samples that have high hematocrit and high glucose, a novel technique is needed in order to maintain similar or better level of accuracy for the known technique in FIG. 4B. Instead of measuring the current value (from the applied voltages of FIG. 4A) at the end of the duration T1 (as in FIG. 4B), the current value for each working electrode is measured with a specific durational offset from the peak of the current transient.

Figure 5A:
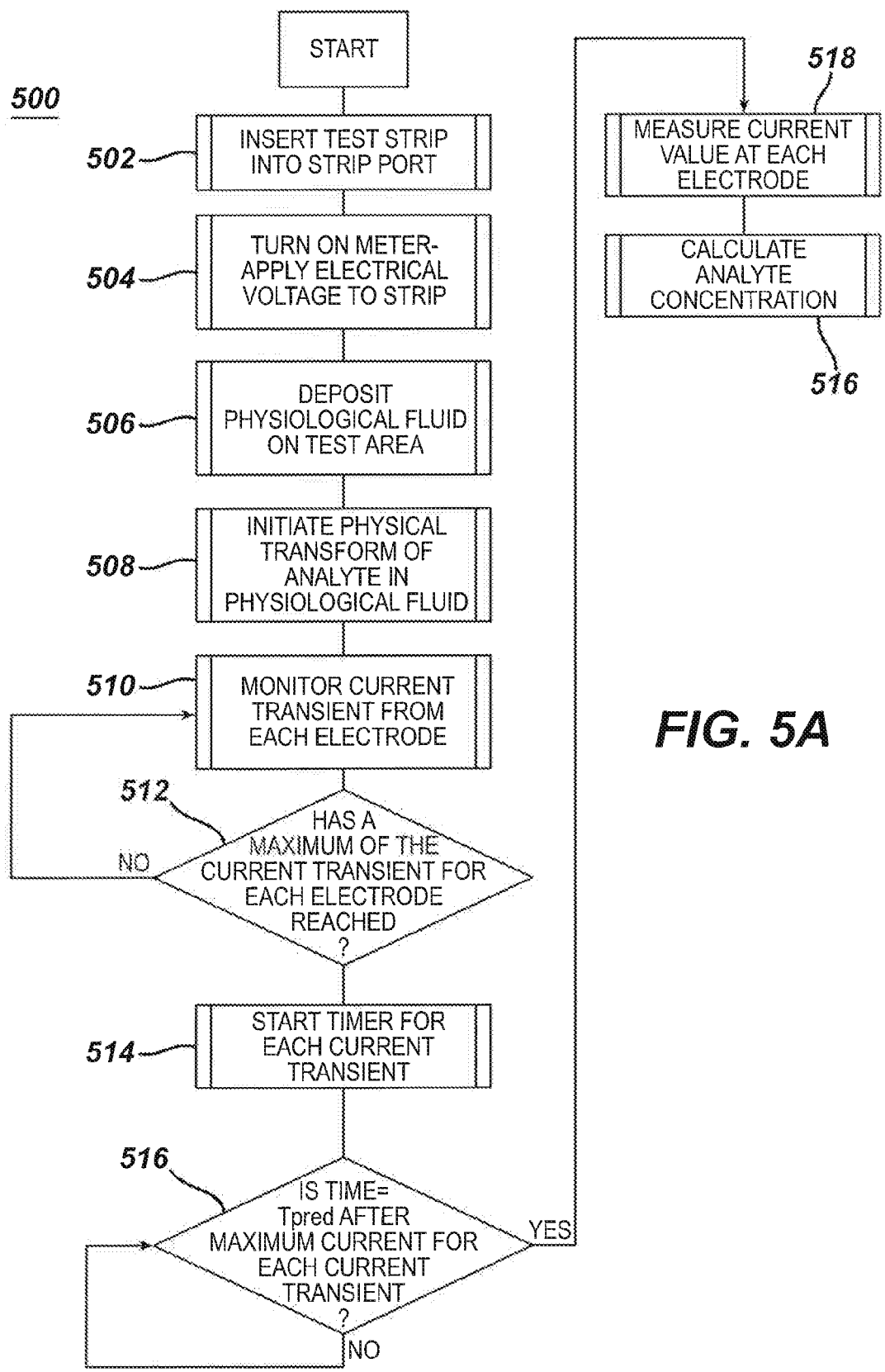
FIG. 5A is a flow chart of an exemplary steps and decisions for the exemplary method implemented in the microcontroller of meter 200.
Figure 5B:
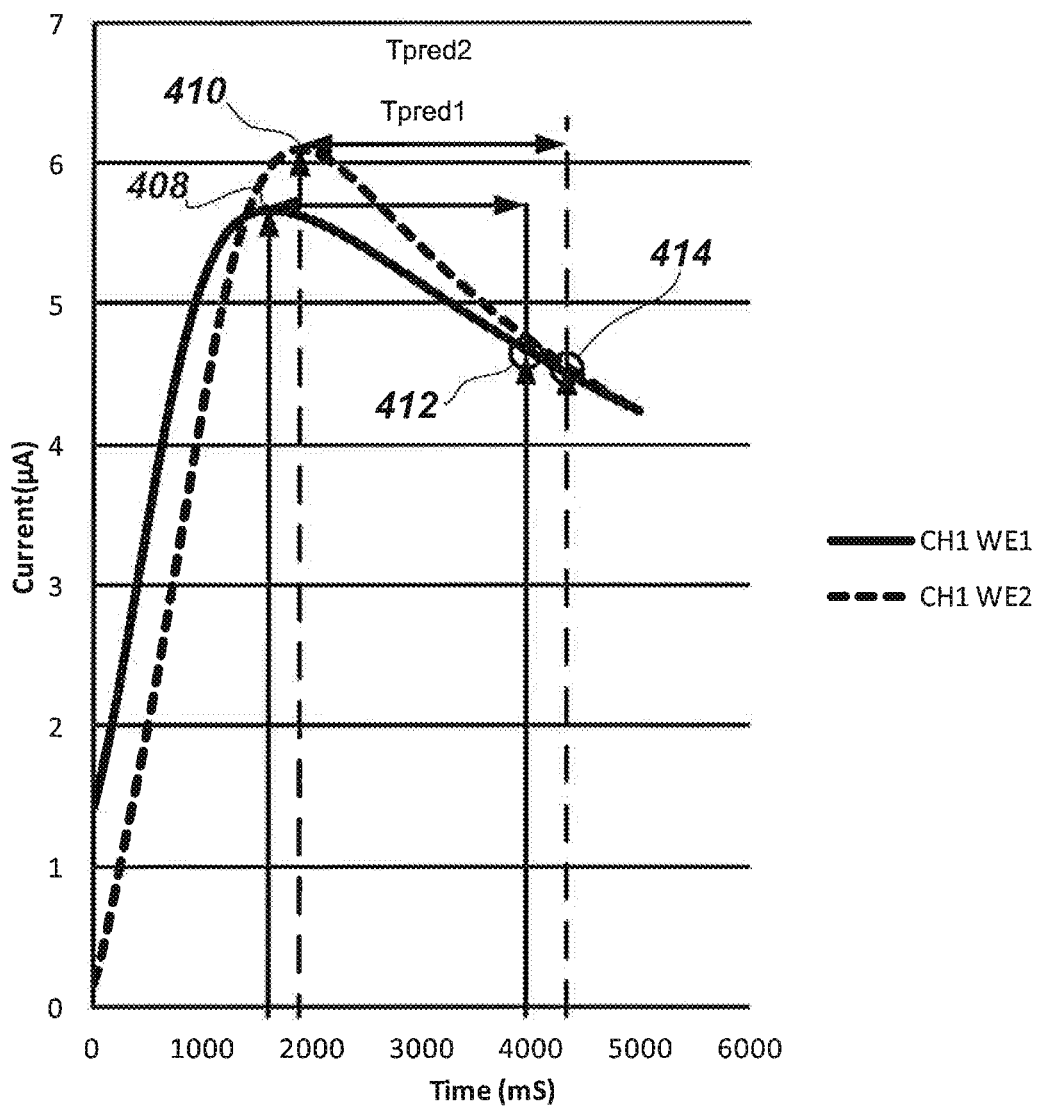
FIG. 5B illustrates the a graph of time over output current and the offset measured current value for the test strip of FIG. 1 with the logic of FIG. 5A.

Specifically, one method 500 is diagrammed in FIG. 5A, which will be described in conjunction with FIG. 5B. In the method 500, a test strip 100' (FIG. 3B) may be inserted into the meter 200, which turns on the meter at step 504. The meter 200 then provides a voltage as shown in FIG. 4A to allow for fluid deposition onto the test strip. Upon deposition of the user physiological fluid on the test area or test chamber of the test strip 100', a short delay is provided to allow for detection of sufficient sample size. Once the meter has decided that the sample size is sufficient, time zero is marked when the current transients start to increase over a certain value to initiate the physical transformation of the analyte into a different physical form by interaction with the reagent at step 508. At step 510, the current transients from respective working electrodes are monitored. A query is provided at step 512 to determine whether a maximum for each current transient has been reached. If true, the logic flows to step 514 which starts a timer to measure the temporal offset from the maximum or "peak" in each of the current transients. A query is provided at step 516 to determine if the timer TIME has reached the temporal offset for each of the working electrodes; in other words, whether TIME=Tpred1 or TIME=Tpred2. If the query at 516 is true, the current value at the time point at which the temporal offset was reached is measured for use in calculating the glucose value in step 520 (using Eq. 3 above). In FIG. 5B, for the current transient 402' of the first working electrode, a durational offset Tpred1 is measured from a peak 408 of current transient 402' at which point 412 in time the current for the first working electrode is measured. Likewise, a durational offset Tpred2 is measured from the peak 410 of the current transient 404' at which point 414 in time the current for the second working electrode is measured. The current values measured at 412 and 414 are used in Eq. 3 along with the specified calibration data to provide for the glucose concentration of the physiological fluid sample. In the preferred embodiments, Tpred1 may have a duration of about 3.3 seconds and Tpred2 may have a duration of about 2.5 seconds.

Figure 6:
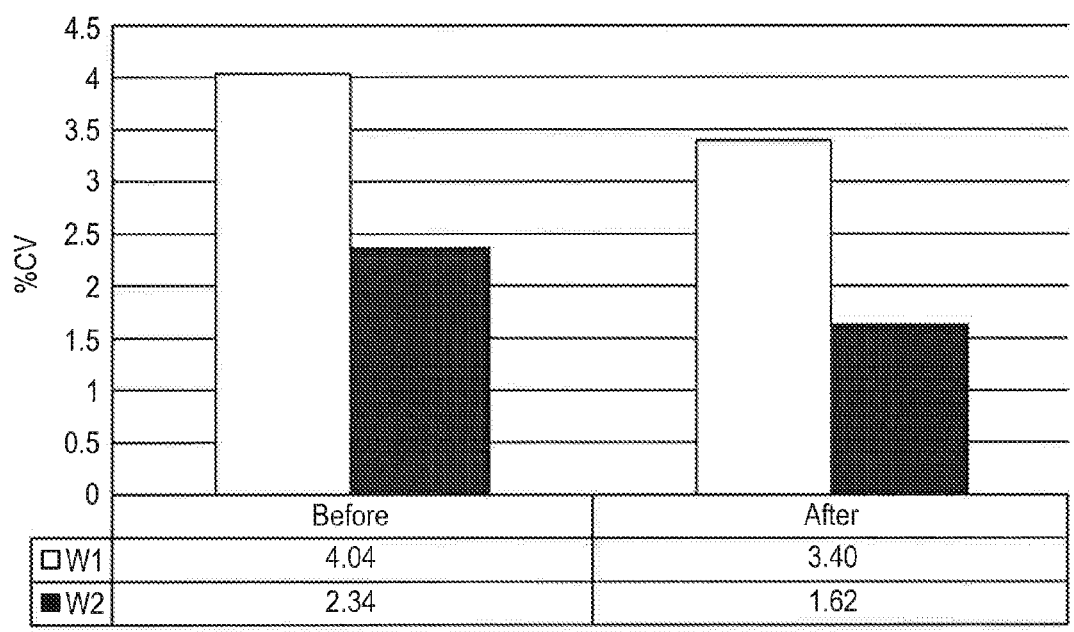
FIG. 6 is a chart showing the coefficient of variation of the known current measurement as compared to that the technique discovered by applicant.

By virtue of the modes of the invention, it is believed that the accuracy of the test strips such as strip 100 and 100', and therefore the accuracy of the analyte measurement system have also increased. Specifically, with reference to FIG. 6, it can be seen that the percent coefficient of variation ("% CV") for both working electrodes for eight strips of the test strip 100' (FIG. 3B) have reduced by 15% from 4.04% to 3.4% for the first working electrode and reduced by 31% from 2.37% to 1.62% for the second working electrode. It is noted that while the time delay from the peak can be about 2.5 seconds to about 3.3 seconds, other durations can also be utilized and its % CV can be analyzed in an iterative manner to achieve the lowest % CV.

While the invention has been described in terms of particular variations and illustrative figures, those of ordinary skill in the art will recognize that the invention is not limited to the variations or figures described. In addition, where methods and steps described above indicate certain events occurring in certain order, it is intended that certain steps do not have to be performed in the order described but in any order as long as the steps allow the embodiments to function for their intended purposes. Therefore, to the extent there are variations of the invention, which are within the spirit of the disclosure or equivalent to the inventions found in the claims, it is the intent that this patent will cover those variations as well.

What is claimed is:

1. A method of determining analyte concentration in physiological fluid, the method comprising:
   providing a reagent disposed between a first electrode and a second electrode;
   depositing a physiological fluid on the reagent;
   causing a physical transformation of an analyte in the physiological fluid into a different from and generating a current transient from each of the first and second electrodes;
   determining a peak in the current transient for each of the first and second electrodes;
   measuring a value of the current transient at a predetermined temporal offset from the peak of each current transient from each of the first and second electrodes in which the temporal offset for the first electrode comprises a first time offset from the peak of the current transient of the first electrode and the temporal offset from the peak of the current transient of the second electrode comprises a second time offset different from the first time offset; and
   calculating the analyte concentration from the measured current values of the first and second electrodes in the measuring step.

2. The method of claim 1, in which a predetermined temporal offset for the first electrode comprises about 3.3 seconds and a predetermined temporal offset for the second electrode comprises about 2.5 seconds.

3. The method of claim 1, in which the measured current value from the first electrode is summed together with the measured current value of the second electrode.

4. The method of claim 1, in which the analyte comprises glucose and the physiological fluid comprises blood.

5. The method of claim 1, in which the first time offset is greater than the second time offset by about 25%.

6. A method of determining analyte concentration in physiological fluid, the method comprising:
   providing a substrate in which a reagent is disposed between a first electrode and a second electrode;
   depositing a physiological fluid onto the reagent;
   applying an electrical potential to the first and second electrodes to transform an analyte in the physiological fluid into a different form and to generate a current transient from each of the first and second electrodes;
   determining a peak in the current transient for each of the first and second electrodes;
   measuring a current value of the current transient at a predetermined temporal offset from the peak of each current transient from each of the first and second electrodes in which the temporal offset for the first electrode comprises a first time offset from the peak of the current transient of the first electrode and the temporal offset from the peak of the current transient of the second electrode comprises a second time offset different from the first time offset; and
   calculating the analyte concentration from the measured current values of the first and second electrodes in the measuring step.

7. The method of claim 6, in which a predetermined temporal offset for the first electrode comprises about 3.3 seconds and a predetermined temporal offset for the second electrode comprises about 2.5 seconds.

8. The method of claim 6, in which the measured current value from the first electrode is summed together with the measured current value of the second electrode.

9. The method of claim 6, in which the analyte comprises glucose and the physiological fluid comprises blood.

10. The method of claim 6, in which the first time offset is greater than the second time offset by about 25%.

11. A glucose measurement system to measure an analyte concentration in physiological fluid of a user, the system comprising:
    a test strip including a first electrode, a second electrode and a reagent layer having a mediator in a test area disposed proximate the first and second electrodes, the electrodes being connected to corresponding contact pads; and
    an analyte meter having a microprocessor and a test circuit in connection with a test strip port that electrically connects the contact pads of the test strip so that, when the test strip is inserted into the test strip port with physiological fluid deposited in the test area, the meter is configured to apply a voltage potential over a duration and measure a current value of a current transient for each of the first electrode and the second electrode at a predetermined duration after a peak of the current transient in which the predetermined duration for the first electrode comprises a first time offset from the peak of the current transient of the first electrode and the predetermined duration from the peak of the current transient of the second electrode comprises a second time offset different from the first time offset, the current value of the current transient for each of the first and second electrodes being representative of the analyte concentration.

12. The method of claim 11, in which a predetermined duration for the first electrode comprises about 3.3 seconds and a predetermined duration for the second electrode comprises about 2.5 seconds.

13. The method of claim 11, in which the measured current value from the first electrode is summed together with the measured current value of the second electrode.

14. The system of claim 11, in which the analyte comprises glucose and the physiological fluid comprises blood.

15. The system of claim 11, in which the first time offset is greater than the second time offset by about 25%.

* * * * *